(12) United States Patent
Zhou et al.

(10) Patent No.: US 6,234,175 B1
(45) Date of Patent: May 22, 2001

(54) SMART OCULAR PLUG DESIGN AND METHOD OF INSERTION FOR PUNCTAL AND INTRACANALICULAR IMPLANTS

(75) Inventors: Stephen Q. Zhou, Irvine; Christopher D. Wilcox, Mission Viejo; Julian Abadia, Foothill Ranch, all of CA (US)

(73) Assignee: Medennium, Inc., Irvine, CA (US)

( * ) Notice: Subject to any disclaimer, the term of this patent is extended or adjusted under 35 U.S.C. 154(b) by 0 days.

(21) Appl. No.: 09/361,729

(22) Filed: Jul. 27, 1999

Related U.S. Application Data (60) Provisional application No. 60/128,274, filed on Apr. 8, 1999, and provisional application No. 60/125,758, filed on Mar. 23, 1999.

(51) Int. Cl.[7] .................................................. A61B 17/00
(52) U.S. Cl. ................................................ 128/887; 604/8
(58) Field of Search ...................... 128/846, 848, 128/858; 604/4, 8, 9, 10

(56) References Cited

U.S. PATENT DOCUMENTS

| D. 295,445 | 4/1988 | Freeman . |
| 3,949,750 | 4/1976 | Freeman . |
| 4,461,295 | 7/1984 | Herrick . |
| 4,660,546 | 4/1987 | Herrick et al. . |
| 5,049,142 | 9/1991 | Herrick et al. . |
| 5,053,030 | 10/1991 | Herrick et al. . |
| 5,163,959 | 11/1992 | Herrick . |
| 5,171,270 | 12/1992 | Herrick . |
| 5,283,063 | 2/1994 | Freeman . |
| 5,417,651 | 5/1995 | Guena et al. . |
| 5,423,777 | 6/1995 | Tajiri et al. . |
| 5,469,867 | 11/1995 | Schmitt . |
| 5,723,005 | 3/1998 | Herrick . |
| 5,741,292 | 4/1998 | Mendius . |
| 5,806,530 | 9/1998 | Herrick . |
| 6,027,470 | * 2/2000 | Mendius ................................ 604/8 |
| 6,082,362 | * 7/2000 | Webb .................................... 604/8 |

* cited by examiner

*Primary Examiner*—Michael A. Brown
(74) *Attorney, Agent, or Firm*—Frost Brown Todd LLC (57) ABSTRACT

An ocular plug design and method of insertion is described for the treatment of dry eye. This ocular plug is a narrow rod-like cylinder of appropriate diameter, which is tapered at one end, for insertion into an ocular channel. The plug is prepared from either (or both) of two specific classes of polymeric materials having both viscous and elastic properties. The first class of polymeric materials have a glass transition temperature ($T_g$) at or below human body temperature (37° C.). The second class of polymeric materials have a melting temperature ($T_m$) at or below human body temperature (37° C.). The plug is stored in a frozen, rigid, elongated state prior to insertion into an ocular channel. Once inserted into an ocular channel, the smart plug responds to an increase in temperature, due to the surrounding physiochemical environment, whereby it becomes soft and the plug subsequently expands to adapt to the size and shape of the patient's punctum or canaliculum. Once the plug expands to the size of the particular ocular channel, the plug is met with a resistance from the surrounding tissue. At this point, expansion of the plug ceases and the plug can effectively block tear drainage through either ocular channel.

45 Claims, 5 Drawing Sheets

GAUGE TOO LARGE

GAUGE PROPER SIZE

GAUGE TOO SMALL

SMART OCULAR PLUG DESIGN AND METHOD OF INSERTION FOR PUNCTAL AND INTRACANALICULAR IMPLANTS

This application is based on U.S. Provisional Patent Application Ser. No. 60/125,758, Zhou and Abadia, filed Mar. 23, 1999, and U.S. Provisional Application Ser. No. 60/128,274, Zhou and Wilcox, filed Apr. 8, 1999.

TECHNICAL FIELD

The present invention generally relates to a removable intraocular plug used to temporarily close the punctal or canalicular opening of the human eye to be utilized, for example, in the treatment of keratoconjunctivitis sicca (dry eye). Specifically, the present invention relates to a method of occluding ocular channels by using materials that can adapt to the size and shape of the individual's punctum or canaliculus by exploiting the rigid, viscous and elastic properties of the material composition.

BACKGROUND OF THE INVENTION

The human eye includes a complex composition in the form of a tear film. Tears include three basic components: (1) lipids; (2) an aqueous layer; and (3) mucin. The absence of any one of these components causes discomfort and can lead to a temporary or permanent condition known as keratitis sicca (or keratoconjuctivitis sicca, often referred to as dry eye). Dry eye can have a variety of causes but is generally attributed to one or two basic malfunctions. First, the tear ducts leading from the lacrimal glands can be clogged or malfunctioning so that an insufficient amount of tears reaches the eye. For many years, this was generally thought to be the main reason for dry eye. Artificial tears were developed in response to this need. However, the relief to patients using these artificial tears is short-lived and treatment must be readministered several times each hour.

More recently, it has been discovered that, with increasing age, dry eye is caused by either insufficient or inadequate tears and tear components or the inability to maintain effective tear film. Accordingly, recent therapies have proceeded on the basis that tear production may be inadequate in some individuals and that a significant percentage of dry eye syndrome can be alleviated by slowing down the drainage of the tears through the lacrimal ducts.

Figure 1:
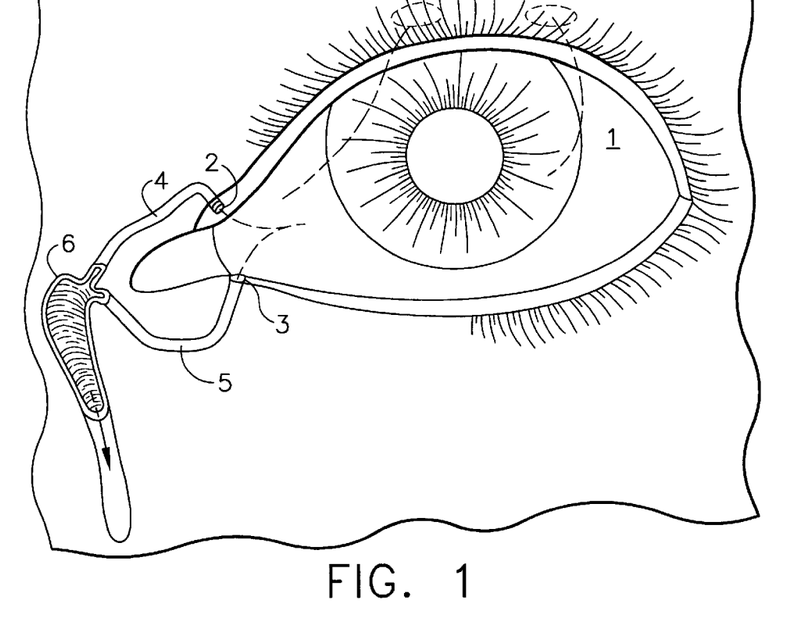
FIG. 1 is a representation of the anatomy of the human eye and associated lacrimal system.

Tears are removed from the eye by draining through the upper and lower punctal openings which lead into the canalicular canals (See FIG. 1). Initial attempts at sealing the puncta and/or the canalicular canals involved stitching the puncta shut or using electrical or laser cauterization to seal the puncta and or canalicular canals. Although such methodology can provide desirable results, the procedure is not reversible without reconstructive surgery. Since it is sometimes difficult to determine whether in a particular patient, the drainage is too great or the tear production is too small, irreversible blockage is not without risk.

One means of temporarily blocking the punctum and canaliculus for the treatment of dry eye is through the use of intracanalicular gelatin implants. *Intracanalicular Gelatin Implants in the Treatment of Kerato-Conjunctivitis Sicca*, Wallace S. Foulds, Brit J. Ophthal (1961) Vol. 45 pp 625–7. Foulds discloses that the occlusion of the lacrimal puncta can be performed by use of and insertion of a fine, water soluble gelatin rod into the punctal openings. The gelatin rod is formed from pure powdered gelatin to which a small quantity of distilled water has been added and is heated in a water bath until the gelatin dissolves and a thick gel results. By dipping a cold glass rod into the prepared gelatin, and withdrawing the same, fine solid rods of gelatin were formed. The gelatin rods were then inserted into the canaliculi to provide a temporary blockage. As such, the gelatin rod implants, although very fragile, provide an alternative means for temporarily blocking the canaliculus.

Figure 2:
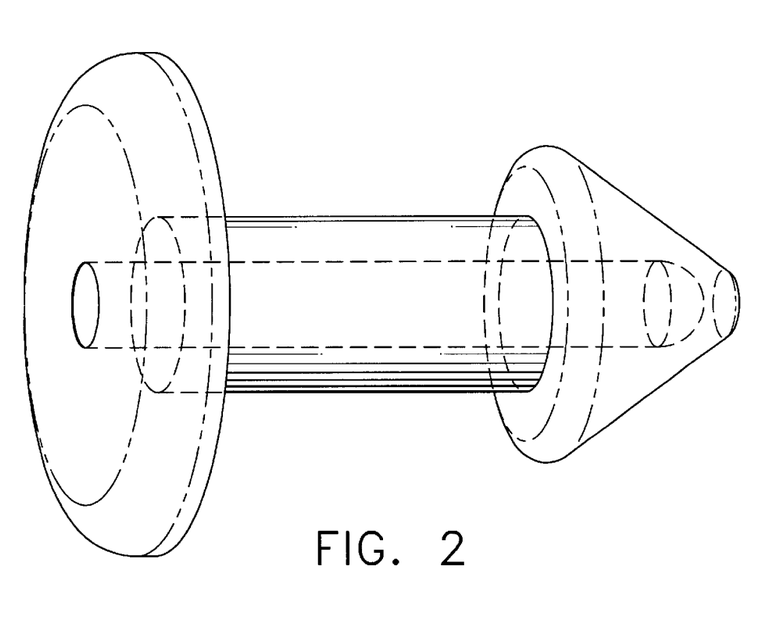
FIG. 2 is a punctum plug used to temporarily close the punctal opening to conserve tears in the human eye for treating dry eye symptoms (see U.S. Pat. No. 3,949,750, Freeman, issued Apr. 13, 1976).

Water-insoluble plugs which can be placed in the punctum openings and into vertical sections of the canalicular canals are disclosed in U.S. Pat. No. 3,949,750, Freeman, issued Apr. 13, 1976. The punctum plug (10) of Freeman is a rod-like plug formed with an oversized tip (11) that dilates and blocks the vertical canaliculus (see FIG. 2). The punctum plug has a relatively large, smooth head portion (12) which functions to prevent the punctum plug from passing into the horizontal portion of the canaliculus. Although these plugs are reversible, they tend to become dislodged quite easily. Further, they are somewhat difficult to insert, and occasionally their size and shape can cause tissue damage during insertion or, if they protrude from the puncta, they can cause irritation to the sclera. The tissue of the punctum can also be damaged by being dilated by the plugs over extended periods of time.

An improvement on the Freeman plugs is disclosed in U.S. Pat. No. 4,959,048, Seder et al., issued Sep. 25, 1990. Seder et al. disclose a preformed plug or channel occluder which is somewhat conical in shape, making it possible to insert the occluder into the opening of the punctum more easily than the devices disclosed by Freeman. Further, Seder et al. disclose that variations in the anatomy of individuals make it desirable to provide a series of occluders in different lengths and/or widths in order to accommodate anatomical differences. Therefore, ophthalmologists need to measure the actual size of the punctal opening to determine the best size of punctum plug to be used for each patient and manufacturers must then provide five or more different sizes of punctum plugs to meet the ophthalmologist's needs.

Figure 3:
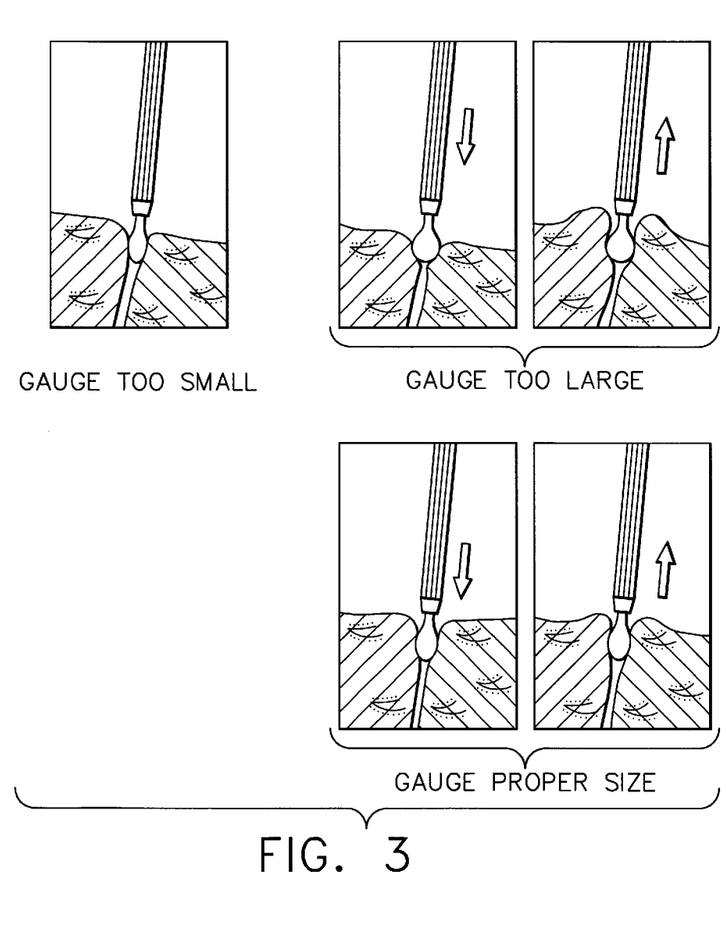
FIG. 3 is a gauge used for measuring the diameter of the patient's punctum.
Figure 4:
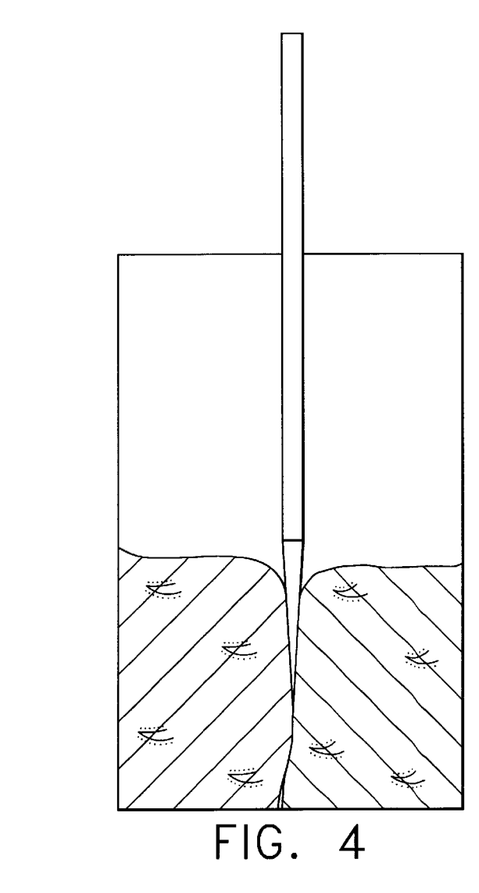
FIG. 4 is a tool used to enlarge the punctum and associated canaliculus prior to inserting the punctum plug.
Figures 5, 6:
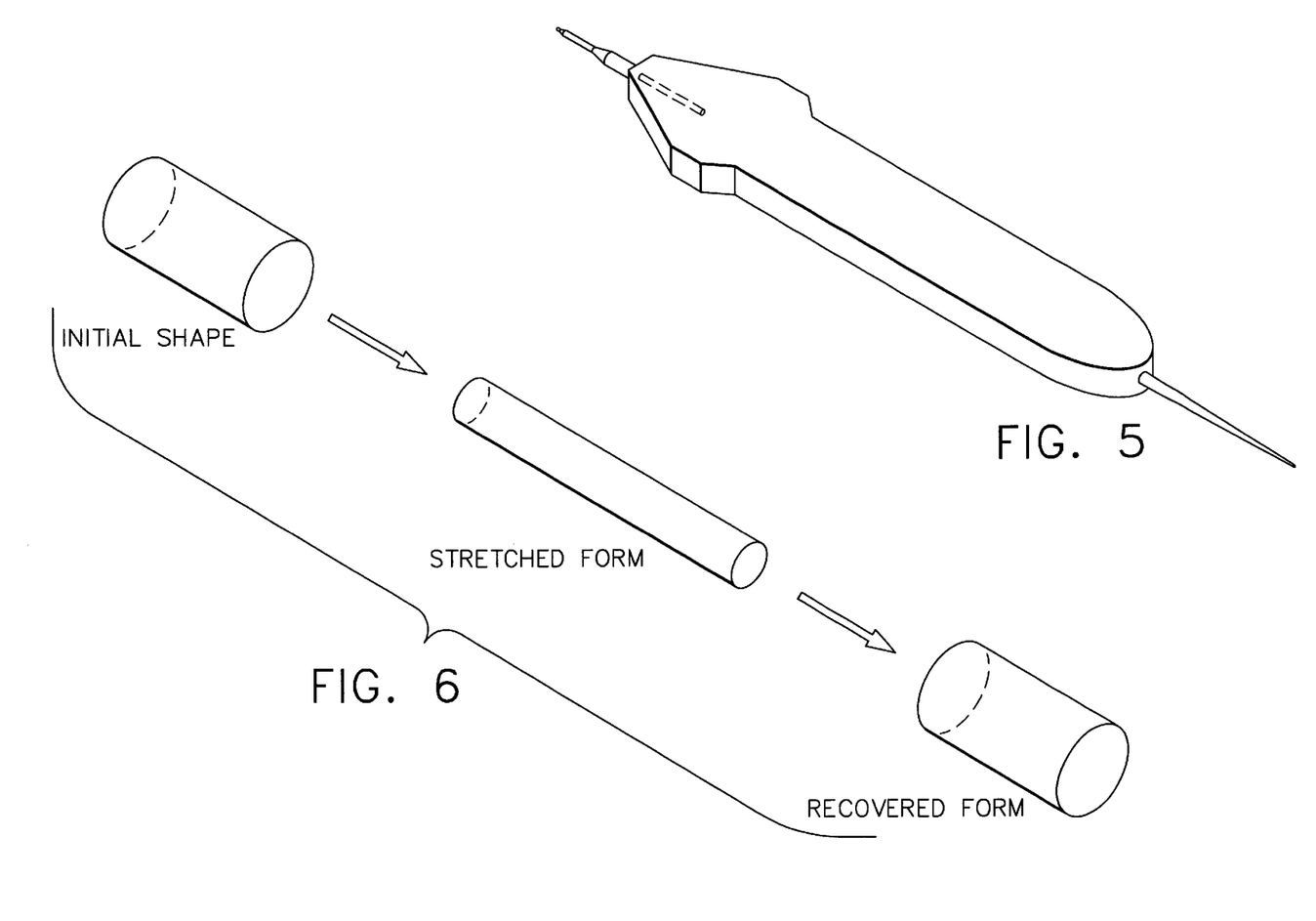
FIG. 5 is an inserter tool used for grasping, manipulating and inserting the plug into the punctal opening.
FIG. 6 shows the shape transformation of the elongated needle-like plug of the present invention returning to its original shape if no restriction force is applied.

Accordingly, using the prior art plugs, doctors must follow a number of procedures that are not only time consuming but also require a high level of skill. First, doctors need to measure each patient's punctum diameter since this size will vary from patient to patient, and for some patients, there will even be variances in punctum size in the left eye versus right eye (see FIG. 3). This is done by inserting a sizing gauge (13) into the punctum (2). An oversized plug will cause the patient discomfort while an undersized plug will fall out of the patient's eye. Second, doctors need to dilate the punctum (2) and quickly insert the plug, usually within 30 seconds or less (see FIG. 4). The dilation needs to be repeated if the plug fails to be inserted within the 30 seconds, and, since the plug is so soft and small, it is often very difficult to complete the insertion within this 30 second time window. FIGS. 4 and 5 show tools which may be used to enlarge the punctum for insertion of the plug.

From the foregoing discussion, there exists a clear need for a new punctal plug design which would greatly simplify or eliminate the current time-consuming surgical dilation and insertion procedures. A "one-size-fits-all" plug design would not only eliminate the need for manufacturers to provide doctors with plugs of various dimensions, but also eliminate the need for doctors to measure the patient's punctal size prior to surgery.

SUMMARY OF THE INVENTION

The above-described objectives are achieved with the method and ocular plug design of the present invention. This invention involves a "smart" punctal and canalicular plug for blocking lacrimal flow through ocular channels. This smart plug is a narrow rod-like cylinder of appropriate diameter for insertion into an ocular channel. It is tapered at one end and is prepared from either (or both) of two specific classes of polymeric materials having both rigid, elastic and viscous properties. The first class of polymeric materials have a glass transition temperature ($T_g$) at or below human body temperature (37° C.). The second class of polymeric materials have a melting temperature ($T_m$) at or below human body temperature (37° C.). The polymeric materials of the present invention can also be the blended with wax-like materials to form a composition with a $T_g$ and/or $T_m$ at or below 37° C. Since the plug is stored in a frozen, rigid, elongated state prior to insertion, doctors should find it easier to insert this plug into the punctum or canaliculus of the eye as compared with a soft plug and the need for a special inserter during surgery is eliminated (see FIG. 5).

Once inserted into an ocular channel, the smart plug responds to an increase in temperature, due to the surrounding physiochemical environment, whereby it becomes soft and the plug subsequently expands to adapt to the size and shape of the patient's punctum or canaliculum. Once the plug expands to the size of the particular ocular channel, the plug is met with a resistance from the surrounding tissue, and at this point, expansion of the plug ceases. This externally applied resistance by the surrounding tissue in turn activates the elastic and viscous properties of the plug which function to fill any void space between the plug and punctum or canaliculus (see FIG. 8). Thus, the plug can effectively block tears from being drained through either ocular channel.

In particular, the present invention relates to a method for inserting a plug into an ocular channel, in which a biocompatible composition is supplied that is rigid at room temperature, becomes elastic when warmed to a temperature above either its melting temperature, $T_m$, or its glass transition temperature, $T_g$, and becomes rigid once again when cooled to temperature below either its $T_m$ or $T_g$. The material for this composition consists of polymeric materials such as homopolymers, cross-linked polymers and copolymers of silicones, acrylic esters, polyurethanes, hydrocarbon polymers, silicone elastomers, and mixtures of these polymeric materials with waxes. This biocompatible composition is then warmed to a temperature at which it becomes elastic and subsequently is formed, through stretching, into a rod having dimensions suitable for insertion into an ocular channel. The resulting composition is allowed to cool and re-solidify in its stretched, rigid form at which point it is inserted into an ocular channel. The composition is then warmed by the body, becoming viscous and elastic, and subsequently conforms to the shape of the ocular channel.

The present invention also relates to a removable rod-like plug for blocking lacrimal flow through the punctum or canaliculus of the human eye. It is constructed from a biocompatible composition that is rigid at room temperature, becomes elastic when warmed to a temperature above either its melting temperature, $T_m$, or its glass transition temperature, $T_g$, and becomes rigid once again when cooled to temperature below either its $T_m$ or $T_g$. Materials suitable for this composition generally consists of polymers, homopolymers, cross-linked polymers and copolymers of silicones, acrylic esters, polyurethanes, hydrocarbon polymers, silicone elastomers, and mixtures of these polymers with waxes. The composition is formed into a cylindrical shape of diameter and length which is sufficient to fully occlude the ocular channel and has a tapered end to facilitate insertion into the punctum or canaliculus. The plug is stretched along its length and maintained in its frozen, elongated form prior to insertion.

DETAILED DESCRIPTION OF THE INVENTION

To facilitate the understanding of the present invention, a brief description of the human eye 1 and the associated lacrimal system showing the paths of the tears from the sources is presented. FIG. 1 illustrates the lacrimal system for a human eye 1. Tears flow into small openings called puncta located in the lids of the eye. Both upper punctum 2 and lower punctum 3 lead to corresponding upper canaliculus 4 and lower canaliculus 5. The upper canaliculus 4 and the lower canaliculus 5 merge into the lacrimal sac 6 from which tears travel into the nasal lacrimal duct 7 and drain into the nose. The majority of the tears drain through the lower punctum 3 via canaliculus into the nasal passage. The implant is to be inserted into either the punctal opening or the horizontal portion of the canaliculus.

Definitions

Throughout the disclosure, unless the context clearly dictates otherwise, the terms "a" "an" and "the" include plural referents. Thus, for example, a reference to "a polymer" includes a mixture of polymers and statistical mixtures of polymers which include different weight average molecular polymers over a range. Reference to an "occluder" includes one or more occluders or plugs, and reference to "ocular channel" includes the punctum and canaliculum.

Unless defined otherwise, all technical terms and scientific terms used herein have the same meaning as commonly understood by one ordinarily skilled in the art to which this invention belongs. Although any methods and materials similar or equivalent to those described herein may be used in the practice or testing of the present invention, preferred methods and materials are described below. All publications mentioned herein are incorporated by reference. Further, specific terminology of particular importance to the description of the invention is defined below.

The terms "occluding" or "blocking" refer to the process of partially and/or completely filling at least a portion or section of an ocular channel, passage, opening, cavity or space with a substance that hinders and/or completely prevents the transport or movement of another substance through the channel. This "other substance" is generally tears. In preferred embodiments, the channel is completely blocked to prevents the flow of tears.

The term "biocompatible" is intended to mean that no acute physiological activity is observed in response to the presence of the material or substance described as possessing such a property. Examples of unacceptable physiological activity would include surface irritation, cellular edema, etc.

The terms "polymer" and "polymeric material" are used interchangeably herein to refer to materials formed by linking atoms or molecules together in a chain to form a longer molecule, i.e., the polymer. The polymers used in the present invention are preferably biologically inert, biocompatible and non-immunogenic. The particularly preferred polymeric materials are biocompatible, non-immunogenic and not subject to substantial degradation under physiological conditions.

The terms "polymer", "polymer composition", "polymeric material", "composition", and "composite" are interrelated. The terms "polymer composition" and "polymeric material" are used interchangeably and refer to either the polymer or polymeric material itself as defined above or a composite as defined below. The term "composite" refers to a combination of a polymer with a biologically inert substance that need not qualify as a "polymer" but may have the special characteristics of having a melting point above body temperature and may have the ability to provide desirable properties to the polymer (such as to toughen or act as a heat sink for the polymer). Examples of these biologically inert substances or waxes are, for example, octadecane or oligomeric polyethylenes.

The term "melting point" ($T_m$) of the polymer refers to the temperature at which the peak of the endotherm rise is observed when the temperature is raised through the first order transition at standard atmospheric conditions. The first order transition is the melting point of the crystalline domains of the polymer. The peak developed in the trace of a differential scanning calorimeter (DSC) analysis experiment has been used to define this transition (see Encyclopedia of Polymer Science and Engineering, $2^{nd}$ edition, vol. 4, pp. 482–519).

The term "glass transition temperature" ($T_g$) refers to the temperature at which the amorphous domains of a polymer take on the characteristic properties of the glassy state-brittleness, stiffness, and rigidity. At the glass transition temperature, the solid, glassy polymer begins to soften and flow (see Encyclopedia of Polymer Science and Engineering, $2^{nd}$ edition, vol. 7, pp. 531–544).

The term "smart plug" and "plug" are used interchangeably and refer to the polymer, polymeric material, polymer composition or composite in its solid elongated form below the crystalline $T_m$ or $T_g$ (i.e. prior to insertion into the ocular channel) and in the shape and dimensions of the channel which it fills.

Main chain crystallizable polymers (MCC polymers) are useful for this invention and are well-known, some of which, are commercially available. These are described by Robert W. Lenz, "Organic Chemistry of Synthetic High Polymers", John Wiley & Sons, New York, 1967, pp. 44–49, incorporated herein by reference. Generally, these polymers are characterized as having crystallizable structures, such as stiff repeating units or stereoregular repeating units, as part of the main polymer chains. The more persistent the crystalline structural units, the higher degree of crystallinity of the polymer.

Side chain crystallizable polymers (SCC polymers) are also particularly useful for this invention and also are well-known, some of which are commercially available. These polymers are described in J. Polymer Sci.: Macromol. Rev. 8:117–253 (1974), the disclosure of which is hereby incorporated by reference. In general, these polymers are characterized as having a crystallizable cluster off to the side of the main backbone and can be made in several configurations, i.e. homopolymers, random copolymers, block copolymers and graft copolymers.

Polymeric Materials

In general, material compositions of the present invention can be divided into two classes. The first class contains at least one component which has a glass transition temperature (Tg) at or below human body temperature (37° C.). The second class contains at least one component which has a melting temperature ($T_m$) at or below human body temperature (37° C.). Compositions containing both the first class and second class can also be used for the present invention as long as either (or both) the $T_g$ or $T_m$ of the mixture is below about 37° C.

The glass transition temperature of a polymer is the temperature above which the polymer is soft and elastic and below which the polymer is hard or glass-like. Examples of suitable $T_g$ polymeric materials include, but are not limited to, silicones, acrylic polymers, polyurethanes, hydrocarbon polymers, copolymers of the foregoing, and any combinations thereof. These polymers may be blended with wax-like materials, such as octadecane, or oligomeric polyethylenes to create a composite that contains both rigid, elastic and viscous properties and has a $T_g$ at or below 37° C. Preferably, the $T_g$-based polymeric material is an acrylic ester and more preferably it is a copolymer of laurylmethacrylate and methylmethacrylate.

Generally speaking, the $T_g$ of a copolymer containing two or more monomers will be dependent on the percentage composition of the monomers. For example poly(methyl methacrylate) (PMMA) has a $T_g$ of 105° C. Therefore, it is soft and rubbery, and it can be molded into various shapes above 105° C. At room temperature, however, PMMA is hard and this is due to the short C-1 side chain. This hardness enhances the elasticity of the copolymer and is the driving force for the stretched polymer to return to its initial shape after the temperature increases above its $T_g$. On the other hand, poly(lauryl methacrylate) (PLMA) has a Tg of −65° C., and is soft at room temperature, due in part to the C-12 side chain. Thus, a copolymer containing various ratios of PMMA and PLMA can be designed to achieve any $T_g$ in the range of −65° C. to 105° C.

For instance, a copolymer in a molar ratio of 40% lauryl methacrylate and 60% methyl methacrylate, as described in Example 1, has a $T_g$ of 19° C. This particular side-chain copolymer has a number of desirable properties for the smart punctal plug design. Because the $T_g$ of this copolymer is 19° C., at room temperature it is elastic and can be stretched. When the stretched sample is placed into ice water for about one minute, it remains in the stretched, rigid form as long as the surrounding temperature is maintained below 19° C. However, those skilled in the art realize that the glass transition temperature for a polymer occurs over a temperature range, possibly 10° C. or even larger, rather than a single sharply defined temperature. Also, since this copolymer has C-12 alkyl side chains, there is a high degree of freedom associated with the various rotational perturbations the molecule may undergo. Such a copolymer is superior to the main chain crystallizable polymers as well as crosslinked polymers since these have much more restricted modes of rotational movement. Thus, the flexibility of the C-12 side chain of the LMA component enables this copolymer to readily conform to the shape of the ocular channel. The MMA component of this copolymer is relatively hard and elastic. This elasticity is the driving force for the stretched plug to return to its initial shape. Additionally, the LMA/MMA copolymer can be crosslinked using appropriate crosslinkers (see Example 2). Crosslinking further enhances the elastic properties of this copolymer. Finally, this copolymer is an acrylic ester and polymers of this chemical composition have been most widely used in ophthalmic implants because of their long-term stability and biocompatability.

A second class of polymers which can also serve as an ideal material for this smart plug design are those polymers which have a $T_m$ lower than about 37° C. The $T_m$ of these polymers is a function of the crystalline structure resulting from the nature of the main chain or side chain. The group of $T_m$ materials includes, but is not limited to, those compositions which have a crystalline structure based upon one or more side chains which contain at least 10 carbon atoms, or alternatively, any compositions whose crystalline structure is a function of the polymeric main chain structure.

Examples of side chain crystalline materials are, but not limited to, homopolymers or copolymers that contain one or more monomeric units (wherein n=at least 1 monomer unit) having the general formula:

wherein

X is H, or a $C_1$–$C_6$ alkyl radical;

R is a linear $C_{10}$–$C_{26}$ alkyl radical.

For example, poly(stearylmethacrylate) (PSMA) is a white solid which has an observed melting temperature of 34° C. (see Table 1). This melting temperature is mainly attributed to the crystalline structure of the polymer due to the presence of the pendant 18-carbon side chain. Upon warming the PSMA up to the human body temperature (ca. 37° C.), this white solid is transformed into a clear elastic polymer. Furthermore, the elastic properties of PSMA can be altered by copolymerization with one or more other monomers. Also, whether the PSMA copolymer becomes more elastic or more rigid than PSMA alone is determined by the nature of the added monomers. Table 1 illustrates the properties of various copolymer compositions of stearylmethacrylate (SMA) with methylmethacrylate (MMA). As illustrated in Table 1, when the percentage of MMA increases in the copolymer composition, the copolymer become more rigid and its elasticity increases. For the present invention, preferably this composition is a copolymer constituting at least 95% SMA/5% MMA, and more preferably 97.5% SMA/2.5% MMA.

TABLE 1

SMA/MMA Polymer Compositions and Their Melting Temperature

| ID | Weight of SMA (grams) | Weight of MMA (grams) | Melting Temperature (° C.) |
| --- | --- | --- | --- |
| PSMA | 1.0 | 0 | 34 |
| 97.5% PSMA | 9.75 | 0.25 | 28 |
| 95% PSMA | 9.50 | 0.50 | 26 |
| 90% PSMA | 9.0 | 1.0 | 22 |
| 80% PSMA | 8.0 | 2.0 | 18 |

(SMA = stearylmethacrylate monomer; MMA = methylmethacrylate monomer)

Examples of the main chain crystallizable materials of the $T_m$ family include, but are not limited to, silicone elastomers derived from the general structure of poly[methyl(3,3,3-trifluoro-propyl)siloxane]. Examples of such silicone elastomers are disclosed in U.S. Pat. No. 5,492,993, Saam et al., issued Feb. 20, 1996, and also described in *Strain-Induced Crystallization in Poly[methyl(3,3,3-trifluoropropyl) siloxane] Networks*, Battjes et al., Macromolecules, 1995, 28, 790–792, both of which are incorporated by reference herein.

Description of the Methodology

As discussed above, it is possible to engineer materials with balanced rigid, elastic and viscous properties. A smart plug made from these materials is elongated at temperatures above its $T_g$ or $T_m$ and the plug subsequently frozen in its elongated form at temperatures below its $T_g$ or $T_m$. Upon insertion into the ocular channel, the plug "senses" an increase in its external environmental temperature. In response to this increase in temperature, the elongated rigid plug becomes soft and rubbery, which in turn triggers the shape recovery motion caused by the elastic properties of the plug material. Once the plug approximately corresponds to the size of the ocular channel, resistance from surrounding tissue stops further expansion of the plug and the plug will "rearrange" itself to the size and the shape of the patient's ocular channel now based upon the inherent viscosity of the composition. It is noted that such movement by the composition due to its viscosity at a molecular level and results from the presence of pendant hydrocarbon side chains on the polymer. Thus, this is a "smart plug" since it is able to adapt to the size and the shape of each patient's ocular channel.

Figures 8, 9:
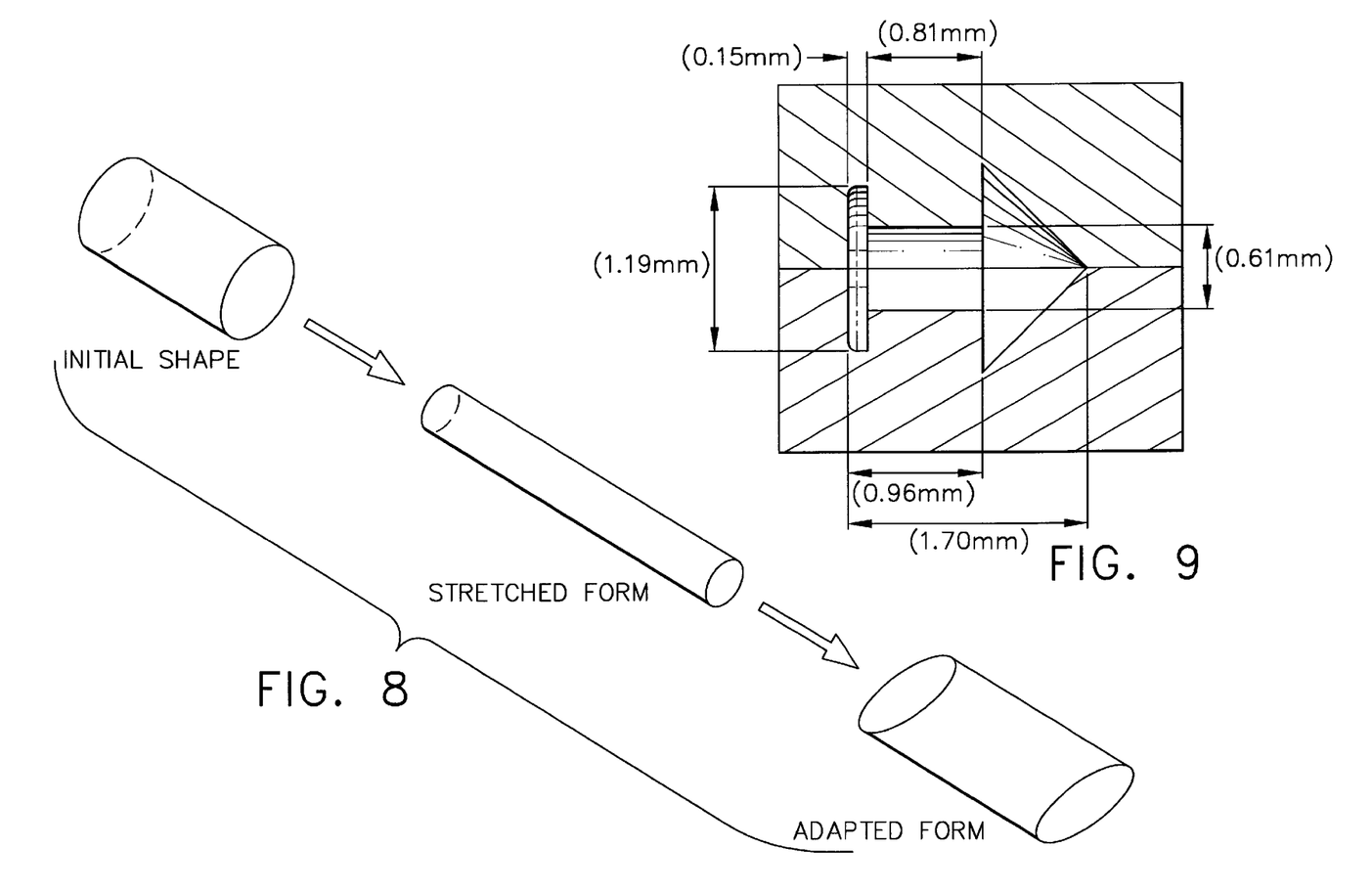
FIG. 8 shows the shape transformation of the elongated needle-like plug of the present invention adapting to its environment when a restriction force is applied.
FIG. 9 shows the shape and dimensions of the Ni—Cu mold used for plug preparation.

When a plug of this new design is fabricated, its initial dimension (15) is designed to fit the large size of the punctum, which is approximately 1 mm to about 5 mm in length and approximately 0.5 mm to a maximum of about 2.5 mm in diameter. This large size punctal plug is then elongated into a thin, needle-like rod (16), at temperatures above the $T_g$ or $T_m$, to a length of about twice that of the initial plug length. The diameter is thus reduced to about 70% or less of its initial diameter. Cooling the elongated plug to temperatures below its $T_g$ or $T_m$ will freeze the needle-like shape as long as the temperature remains below the $T_g$ or $T_m$ of the plug material. Consequently, doctors can simply insert the elongated plug into an ocular channel. Since this elongated plug is rigid and has a reduced diameter, there is no need to dilate the punctum as disclosed in prior art (for example, see U.S. Pat. No. 3,949,750, Freeman, issued Apr. 13, 1976). Upon warming, this plug becomes soft and rubbery and the elastic component of the plug material will cause the elongated needle-like solid rod to return to its original larger size and shape (15) if no restriction force is applied to the plug. This shape transformation is illustrated in FIG. 6. FIG. 8 shows the initial shape of the plug (15), the elongated shape (16) after it is stretched and frozen, and the adaptation of the plug to the shape of the punctum (17) after the plug is inserted and warmed to body temperature.

However, for in vivo applications, the surrounding ocular tissue will supply a resisting force to the expanding plug once the plug reaches the size of the particular ocular channel in which it resides, achieving a "one-size-fits-all" plug design. Where and when the plug stops expanding is controlled by the balance between the elastic properties of the plug material and the resistance supplied by the surrounding tissue. In terms of polymer rheology, how well the needle-like rod will adapt to the size and shape of the patient's punctum or canaliculus is determined by the ratio of the elastic and viscous components of the polymeric material. The higher the percentage of the viscous component, such as a C-18 side-chain crystallizable polymer, the more likely the plug will conform to the size and the shape of the ocular channel. In order to provide a sufficient quantity of the viscous component to the polymer composition, the side chain crystallizable polymer should be a $C_{10}$ or higher carbon radical; alternatively, if the composition is a copolymer, 50% of the copolymer composition should contain a $C_{10}$ or higher side chain crystallizable polymer.

In typical applications, the use of homopolymers or copolymers (see Table 1) is routinely used for the smart punctal plug design. For example, a solid rod of the copolymer polystearylmethacrylate/methylmethacrylate (1 mm in diameter, 100 mm in length) is warmed to a temperature above its $T_m$ so that it becomes soft. The rod is subsequently stretched to approximately 0.5 mm in diameter and 300 mm in length, and immersed in ice water. After approximately 1 minute of cooling, the rod will remain in its elongated, rigid form. The rod is maintained at a temperature below its $T_m$ until it becomes opaque, indicating that crystallization of the polymer side chain has occurred. At this point, the stretched rod is almost as hard as a solid crystal. This hardness is required for ease of insertion of the rod into the ocular channels. This elongated rod is then cut into pieces which are 6 mm in length. One end of shortened rod is then sharpened to form a tapered point for ease of insertion. If necessary, a flared neck may be also formed at the opposite end of the rod. A total of approximately 45–50 pieces may be formed in this manner. Upon insertion, the rod is warmed by the surrounding body tissue, and the elongated form of the rod will begin to deform, and take on the shape of the ocular channel for occlusion. The final dimensions of the plug will conform to the size and shape of the individual's ocular channel.

Finally, if doctors wish to remove the punctal plug, an ice patch is applied to the outside area surrounding the punctum. In a few minutes, the smart punctal plug becomes hard again. Doctors can use regular tools, such as forceps, to grasp the plug and extract it. This procedure eliminates any risks involved in removing a soft plug hat may break into small pieces when pulled out using forceps.

EXAMPLES

In order that the present invention may be more fully understood, the following examples and other comparative results are given by way of illustration only and are not intended to be limiting.

Example 1

Figure 7:
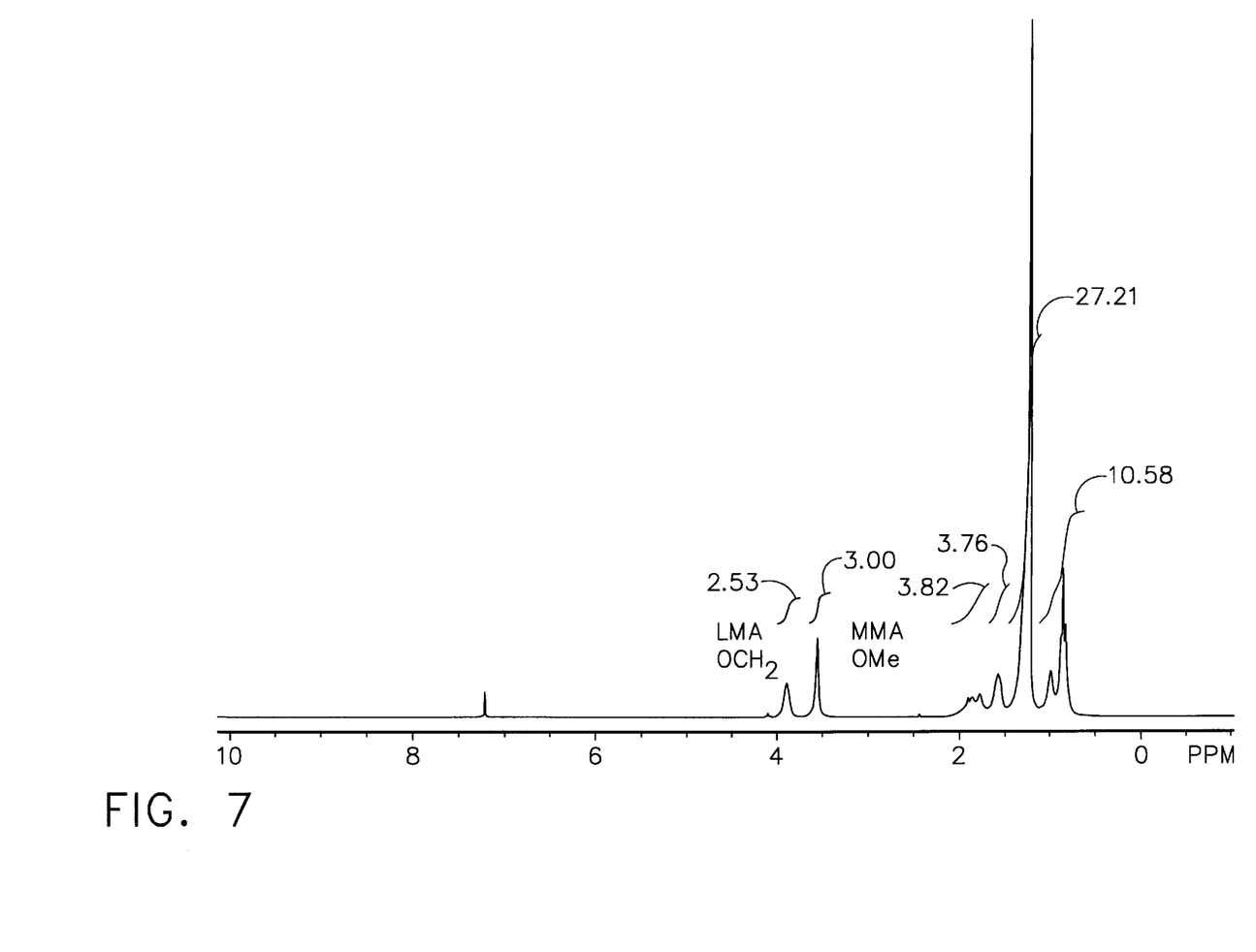
FIG. 7 is the $^1H$ NMR spectrum of the product resulting from the co-polymerization of laurylmethacrylate with methylmethacrylate.

To a round-bottomed flask, under $N_2$ atmosphere, equipped with a magnetic stirring bar, is added a mixture of 8.89 g of methylmethacrylate, 15.39 g of laurylmethacrylate, and 0.02 g of benzoyl peroxide. The reaction mixture is heated to approximately 100–110° C. After approximately 20 minutes, evolution of $O_2(g)$ is observed, indicating decomposition of the benzoyl peroxide for initiation of the polymerization reaction. After about 5 minutes from the initial evolution of gas, the reaction mixture becomes viscous, indicating the polymerization has started. Before the reaction mixture becomes too viscous, it is transferred to a Teflon plate equipped with a Teflon gasket. A second Teflon plate is then placed on top of the reaction mixture in order to sandwich the polymer between the two Teflon plates. This set of Teflon plates containing the polymer is then placed in between two glass plates, clamped together, and heated in an oven at 90° C. for 15 h. The temperature is then raised to 130° C. for an additional 3 h. At this point, the glass plates containing the polymer are removed from the oven and produce a transparent elastic sheet of the polymer measuring 3.5 inches×4.5 inches. The polymer has a $T_g$ of 19° C. Mechanical properties of the polymer as measured by ASTM D412 are as follows: Tensile strength: 292 psi; Elongation at break: 531%. Since there are no crosslinkers in this composition, the copolymer is soluble in organic solvents, such as chloroform. By $^1H$ NMR, there are no visible signals caused by the vinyl protons, indicating the polymerization is complete (see FIG. 7). Quantitative analysis of $^1H$ NMR indicates that there is approximately 56% mole percentage of lauryl methyacrylate in this copolymer. This copolymer is a thermoelastomer. A unique characteristic for a thermoelastomer is that it can be injection molded at temperatures above its class transition temperature.

Example 2

The same procedure as in Example 1 is followed with the exception of the reactants: 7.8 g of methylmethacrylate is combined with 13.2 g of laurylmethacrylate, and 0.07 g of a crosslinker, ethylene dimethacrylate, is also added to the reaction mixture. The copolymerization is initiated by benzoyl peroxide. The resulting copolymer has a $T_g$ of 9° C. Due to its crosslinking, this copolymer is not soluble in any organic solvents. In fact, due to the high degree of crosslinking, this copolymer behaves like a typical elastomer with a very small viscosity component. Mechanical properties of the polymer as measured by ASTM D412 are as follows: Tensile strength: 550 psi; Elongation at break: 488%.

Example 3

The same procedure as in Example 1 is followed with the following exceptions: a mixture of 9 g of stearylmethacrylate is combined with 1 g of methylmethacrylate, using benzoyl peroxide as the initiator, and the reaction mixture is heated to 110° C. for 15 h. The melting temperature of the resulting copolymer is 22° C. (see Table 1). The other compositions listed in Table 1 are also prepared in a similar fashion.

Example 4

To a round bottom flask, under a $N_2$ atmosphere, is added a mixture of 9 g stearylmethacrylate, 1 g of methylmethacrylate and 0.02 g of benzoyl peroxide. The reaction mixture is gently stirred until all the benzoyl peroxide is dissolved. The resulting solution is injected into a glass capillary tube (ca. 1 mm in diameter and 100 mm in length) using a 100 µL syringe. The glass capillary is sealed and heated to 100° C. overnight. The tube is then cooled to 10° C. for 15 h during which time the copolymer turns white due to crystallization of the side chain structure. The glass tube is carefully broken to yield a solid copolymer measuring ca. 1 mm in diameter and 100 mm in length.

The resulting copolymer rod is warmed to 40° C. in a water bath, stretched to approximately 300 mm in length and then cooled for 1 minute in an ice bath to allow the stretched rod to re-solidify. The stretched rod is subsequently cut into pieces 6 mm in length with one end sharpened and the opposing end optionally having a flared neck.

Example 5

The same procedure as in Example 4 with the following exceptions: 0.02 g of ethylene dimethacrylate is added as a crosslinker. The addition of the crosslinker makes this copolymer more rigid and therefore more elastic so that it has a better ability to recover from the stretched solid form back to its initial shape. Also, the crosslinking of the copolymer reduces the viscous properties of the copolymer so that a larger externally applied force is needed in order to stop the shape recovery process. Therefore, by controlling the amount of crosslinking agent used in a composition, it is possible to achieve a balance of properties for desirable viscous and elastic characteristics.

Example 6

Preparation of copolymer of 62% cis- and 38% trans-isomers of 1,3,5-trimethyl-1,3,5-tris(3',3',3'-trifluoropropyl) cyclotrisiloxane and curing (crosslinking):

(1) Preparation of the initiator: In a 10 mL round-bottom flask, under Ar, equipped with magnetic stir bar is added 0.5 g diphenyldihydroxysilane, 5 µL of styrene and 4 mL of dry THF. At this point, 2.5M n-butyllithium (in hexanes) is added dropwise until the reaction mixture becomes yellow in color (ca. 1.8 mL of n-butyllithium was added).

(2) Polymerization: In a 50 mL round-bottom flask, under Ar, is added 12.4 g of 1,3,5-trimethyl-1,3-5-tris(3',3',3'-trifluoropropyl)cyclotrisiloxane (with 62% cis isomer and 38% trans isomer) in 12 mL of dry THF. To the siloxane is added dropwise 0.7 mL of the freshly prepared initiator solution. The reaction mixture is stirred at room temperature for 3 h. At this point a mixture of 0.5 mL of dimethylvinylchlorosilane and 0.5 ml of triethylamine is added and the reaction mixture stirred for an additional 5.5 h. At this point, 25 mL of $H_2O$ is added to the solution and after work-up of this reaction mixture, a copolymer with an average molecular weight of 74,200 and number average molecular weight of 49,600 is obtained. DSC experiments indicate that the cis-enriched copolymer has a $T_m$ of 12° C. and a $T_g$ of −69° C.

(3) Curing: To 0.2 g of the 62% cis- and 38% trans-isomers of poly-1,3,5-trimethyl-1,3,5-tris(3',3',3'-trifluoropropyl)trisiloxane is added 8 µL of tetrakis(dimethylsiloxyl)siloxane and 2 drops of a Pt catalyst. The reaction mixture is stirred for 5 minutes, transferred to a glass capillary tube and sealed. The tube is placed in an oven at 100° C. for 15 h and subsequently cooled in an ice water bath until the silicone hardens, as indicated by it turning slightly cloudy. The glass tube is carefully broken to yield a solid copolymer measuring ca. 1 mm in diameter and 100 mm in length.

Example 7

The following copolymers are prepared as described in Example 4.

|    | BhMA | LMA | MMA  | SMA   | TFEMA | EGDMA | BaSO$_4$ | SiO$_2$ | PF Wax | MC Wax |
|----|------|-----|------|-------|-------|-------|----------|---------|--------|--------|
| 1  | —    | —   | 10%  | 90%   | —     | —     | —        | —       | —      | —      |
| 2  | 80%  | —   | 20%  | —     | —     | —     | —        | —       | —      | —      |
| 3  | —    | —   | 15%  | 85%   | —     | —     | —        | —       | —      | —      |
| 4  | —    | —   | 15%  | 85%   | —     | —     | —        | —       | —      | —      |
| 5  | —    | 50% | 50%  | —     | —     | —     | —        | —       | —      | —      |
| 6  | —    | —   | 10%  | 90%   | —     | —     | —        | —       | —      | —      |
| 7  | —    | —   | 10%  | 90%   | —     | —     | —        | —       | —      | —      |
| 8  | —    | 50% | 50%  | —     | —     | —     | —        | —       | —      | —      |
| 9  | —    | —   | 50%  | 50%   | —     | —     | —        | —       | —      | —      |
| 10 | —    | —   | 9.8% | 88.2% | —     | 2.0%  | —        | —       | —      | —      |
| 11 | —    | —   | 9.5% | 85.7% | —     | 4.8%  | —        | —       | —      | —      |
| 12 | —    | —   | 10%  | 90%   | —     | —     | —        | —       | —      | —      |
| 13 | —    | —   | 10%  | 89.8% | —     | 0.2%  | —        | —       | —      | —      |
| 14 | —    | —   | 10%  | 89.5% | —     | 0.5%  | —        | —       | —      | —      |
| 15 | —    | —   | —    | 100%  | —     | —     | —        | —       | —      | —      |
| 16 | —    | —   | 5%   | 95%   | —     | —     | —        | —       | —      | —      |
| 17 | —    | —   | —    | 90%   | —     | —     | 10%      | —       | —      | —      |
| 18 | —    | —   | —    | 90%   | 10%   | —     | —        | —       | —      | —      |
| 19 | —    | —   | —    | 100%  | —     | —     | —        | —       | —      | —      |
| 20 | —    | —   | —    | 95%   | —     | —     | —        | 5%      | —      | —      |
| 21 | —    | —   | —    | 95%   | —     | —     | —        | 5%      | —      | —      |
| 22 | —    | —   | —    | 90%   | —     | —     | —        | —       | 10%    | —      |
| 23 | —    | —   | —    | 95%   | —     | —     | —        | —       | —      | 5%     |

BhMA: Behenyl methacrylate; LMA: Laurylmethacrylate; MMA: Methylmethacrylate; SMA: Stearylmethacrylate; TFEMA: trifluoroethyl methacrylate; EGDMA: ethyleneglycol dimetharylate; BaSO$_4$ is added for imaging by x-ray analysis; SiO$_2$ is fumed silica used to increase tensile strength; PF Wax is paraffin wax with a melting temperature of 66° C.; MC Wax has a melting point of 93° C.

Example 8

For all of the polymers prepared which have the requisite $T_g$ or $T_m$ values, the method for making and using the plug is as follows: A rod of solid copolymer prepared according to the procedures described in Example 4 is warmed to above 37° C. so that it becomes soft. The rod is then stretched to approximately 5 mm in length and about 0.5 mm in diameter. The stretched rod is immersed into an ice water bath while maintaining the stretching force for approximately 5 minutes. At this point, the rod is removed from the ice water bath and maintained at a temperature below its $T_m$ or $T_g$. One end of the rod is mechanically sharpened to form a tapered point for ease of insertion into the ocular channel. Optionally, a flared neck may be formed at the opposite end the rod. This tapered portion of this plug (rod) is then inserted into the patient's ocular channel using forceps to hold onto the flared end portion of the of the plug.

Example 9

Using the method of polymer preparation as described in Example 4, the resulting solution is injected into a Ni—Cu mold having a shape and dimensions as shown in FIG. 9. The overall plug length is approximately 1.7 mm, with the body of the plug being 1.02 mm in length, the sharpened tip approximately 0.68 mm in length and the flared neck approximately 0.15 mm in length. The diameter of the body of the plug is approximately 0.61 mm, and the tip and flared neck of the plug are both approximately 1.19 mm in diameter. The mold is sealed and heated to 100° C. overnight and then cooled to 10° C. for 15 h during which time the copolymer turns white due to crystallization of the side chain structure. The mold is then opened to obtain the plug. This plug is subsequently warmed to 40° C., stretched to 40 mm in length and immersed in ice water for 1 minute to re-solidify the plug. At this point, the stretched plug is stored at a temperature below its $T_m$ prior to insertion into the ocular channel.

What is claimed is:

1. A method for inserting a plug into an ocular channel, comprising the steps of:
   (a) providing a biocompatible composition which:
      i. is rigid at room temperature;
      ii. becomes elastic when warmed to a temperature above its melting temperature, $T_m$;
      iii. becomes rigid again when cooled to temperature below its $T_m$; and
      iv. comprises a material selected from the group consisting of polymeric materials and mixtures of polymeric materials and waxes;
   (b) warming said composition to a temperature at which it becomes elastic;
   (c) forming said composition into dimensions suitable for insertion into an ocular channel;
   (d) allowing said composition to cool and re-solidify in its stretched form;
   (e) inserting said stretched, rigid composition into an ocular channel;
   (f) allowing said composition to warm to the body's temperature thereby becoming elastic and conforming to the shape of the ocular channel.

2. The method of claim 1 wherein said composition conforms to the shape of the ocular channel in from about 1 second to about 120 seconds after it has been inserted.

3. The method of claim 1 wherein said polymeric material is selected from the group consisting of polymers, homopolymers, cross-linked polymers and copolymers of acrylic esters, silicone elastomers, and combinations thereof.

4. The method of claim 3 wherein said polymeric material is a side-chain crystallizable polymer which comprises an acrylic ester of the formula:

wherein
X is H, or a $C_1$–$C_6$ alkyl radical;
R is a linear $C_{10}$–$C_{26}$ alkyl radical.

5. The method of claim 3 wherein said polymeric material is a main-chain crystallizable polymer comprising the silicone elastomer stereoregular poly[methyl(3,3,3-trifluoropropyl)siloxane].

6. The method of claim 3 wherein said polymeric material in its stretched form is in the shape of a cylindrical rod-shaped implant which is tapered at one end to facilitate insertion into the ocular channel.

7. The method of claim 6 wherein said implant has a length of from about 1 mm to about 5 mm and a diameter of from about 0.5 mm to about 2.5 mm prior to stretching.

8. The method of claim 6 wherein said implant in its stretched form has a length of from about 3 mm to about 20 mm and a diameter of from about 0.25 mm to about 1.25 mm.

9. The method of claim 8 wherein said polymeric material comprises poly(stearyl methacrylate).

10. The method of claim 1 wherein said composition has a $T_m$ of less than about 37° C.

11. The method of claim 3 wherein said implant is adapted for insertion into the punctum or the canaliculus.

12. A method for inserting a plug into an ocular channel, comprising the steps of:
   (a) providing a biocompatible composition which:
      i. is rigid at room temperature;
      ii. becomes elastic when warmed to a temperature above its glass transition temperature, $T_g$;
      iii. becomes rigid again when cooled to temperature below its $T_g$; and
      iv. comprises a material selected from the group consisting of polymeric materials and mixtures of polymeric materials and waxes;
   (b) warming said composition to a temperature at which it becomes elastic;
   (c) forming said composition into dimensions suitable for insertion into an ocular channel;
   (d) allowing said composition to cool and re-solidify in its de-formed state;
   (e) inserting said stretched, rigid composition into an ocular channel;
   (f) allowing said composition to warm to the body's temperature thereby becoming elastic and conforming to the shape of the ocular channel.

13. The method of claim 12 wherein said composition fills and occludes the ocular channel in about 1 minute to about 7 minutes after it has been inserted.

14. The method of claim 13 wherein said polymeric material is selected from the group consisting of polymers, homopolymers, cross-linked polymers and copolymers of silicones, acrylic esters, polyurethanes, hydrocarbon polymers and combinations thereof.

15. The method of claim 14 wherein said polymeric material is an acrylic ester.

16. The method of claim 14 wherein said polymeric material in its stretched form is in the shape of a cylindrical rod-shaped implant which is tapered at one end to facilitate insertion into the ocular channel.

17. The method of claim 16 wherein said implant has a length of from about 1 mm to about 5 mm and a diameter of from about 0.5 mm to about 2.5 mm prior to stretching.

18. The method of claim 16 wherein said implant in its stretched form has a length of from about 3 mm to about 20 mm and a diameter of from about 0.25 mm to about 1.25 mm.

19. The method of claim 18 wherein said implant is comprised of a copolymer of polymethylmethacrylate and polylaurylmethacrylate.

20. The method of claim 12 wherein said composition has a $T_g$ of less than about 37° C.

21. The method of claim 14 wherein said implant is adapted for insertion into the punctum or the canaliculus.

22. A removable rod shape plug for blocking lacrimal flow through the punctum or canaliculus of the human eye comprising a biocompatible composition which:
   a) is rigid at room temperature;
   b) becomes elastic when warmed to a temperature above its melting temperature, $T_m$;
   c) becomes rigid again when cooled to temperature below its $T_m$;
   d) comprises a material selected from the group consisting of polymeric materials, waxes, and mixtures thereof;
said composition being formed into a cylindrical shape of diameter and length which is sufficient to fully occlude the ocular channel and having a tapered end to facilitate insertion into the punctum or canaliculus; said plug being stretched along its length and frozen in said elongated form.

23. The plug of claim 22 wherein said polymeric material is selected from the group consisting of polymers, homopolymers, cross-linked polymers and copolymers of acrylic esters, silicone elastomers and combinations thereof.

24. The plug of claim 23 wherein said polymeric material has a $T_m$ of less than about 37° C.

25. The plug of claim 24 wherein said polymeric material is a side-chain crystallizable polymer which comprises an acrylic ester of the formula:

wherein
   X is H or a $C_1$–$C_6$ alkyl radical;
   R is a linear $C_{10}$–$C_{26}$ alkyl radical.

26. The plug of claim 24 wherein said polymeric material is a main-chain crystallizable polymer comprising stereoregular poly[methyl(3,3,3-trifluoropropyl)siloxane].

27. The plug of claim 24 wherein said polymeric material is poly(stearyl methacrylate).

28. A method for removing the plug of claim 22 from the ocular channel by lowering the temperature of the area surrounding the ocular channel to below the $T_m$ of the material, in order to cause the material to become rigid to aid in excision.

29. A removable rod shape plug for blocking lacrimal flow through the punctum or canaliculus of the human eye comprising a biocompatible composition which:
   a) is rigid at room temperature;
   b) becomes elastic when warmed to a temperature above its glass transition temperature, $T_g$;
   c) becomes rigid again when cooled to temperature below its $T_g$;
   d) comprises a material selected from the group consisting of polymeric materials, waxes, and mixtures thereof;
said composition being formed into a cylindrical shape of diameter and length which is sufficient to fully occlude the ocular channel and having a tapered end to facilitate insertion into the punctum or canaliculus; said plug being stretched along its length and frozen in said elongated form.

30. The plug of claim 29 wherein said polymeric material is selected from the group consisting of polymers, homopolymers, cross-linked polymers and copolymers of silicones, acrylic esters, polyurethanes, hydrocarbon polymers and combinations thereof.

31. The plug of claim 30 wherein said polymeric material has a $T_g$ of less than about 37° C.

32. The plug of claim 31 wherein said polymeric material is an acrylic ester.

33. The plug of claim 32 wherein said polymeric material is a copolymer of polymethylmethacrylate and polylaurylmethacrylate.

34. A method for removing the plug of claim 29 from the ocular channel by lowering the temperature of the area surrounding the ocular channel to below the $T_g$ of the material, in order to cause the material to become rigid to aid in excision.

35. A process for manufacturing punctum plugs or intracanalicular plugs comprising the steps of:
   (a) polymerizing a material in the shape of a cylindrical rod which:
      i. is rigid at room temperature;
      ii. becomes elastic when warmed to a temperature above its melting temperature, $T_m$;
      iii. becomes rigid again when cooled to a temperature below its $T_m$;
      iv. has a diameter of at least 0.5 mm and a length sufficient to form two or more plugs from the same rod;
      v. comprises a material selected from the group consisting of polymeric materials and mixtures of polymeric materials and waxes;
   (b) stretching said rod at a temperature above its $T_m$ to a final length which is at least twice that of its initial length;
   (c) allowing said stretched rod to cool to a temperature below its $T_m$ and re-solidify in its stretched form;
   (d) cutting said stretched rod to an appropriate length so that at least two plugs can be fashioned from the same rod;
   (e) sharpening one end of said stretched rod so that it is tapered.

36. The process of claim 35 wherein said polymeric material is selected from the group consisting of polymers, homopolymers, cross-linked polymers and copolymers of acrylic esters, silicone elastomers and combinations thereof.

37. The process of claim 36 wherein said polymeric material is a side-chain crystallizable polymer which comprises an acrylic ester of the formula:

wherein
   X is H or a $C_1$–$C_6$ alkyl radical;

R is a linear $C_{10}$–$C_{26}$ alkyl radical.

38. The process of claim 37 wherein said polymeric material is poly(stearyl methacrylate).

39. The process of claim 36 wherein said polymeric material is a main-chain crystallizable polymer comprising stereoregular poly[methyl(3,3,3-trifluoropropyl)siloxane].

40. The process of claim 35 wherein said polymeric material has a $T_m$ of less than about 37° C.

41. A process for manufacturing punctum plugs or intracanalicular plugs comprising the steps of:
   (a) polymerizing a material in the shape of a cylindrical rod which:
      i. is rigid at room temperature;
      ii. becomes elastic when warmed to a temperature above its glass transition temperature, $T_g$;
      iii. becomes rigid again when cooled to a temperature below its $T_g$;
      iv. has a diameter of at least 0.5 mm and a length sufficient to form two or more plugs form the same rod;
      v. comprises a material selected from the group consisting of polymeric materials and mixtures of polymeric materials and waxes;
   (b) stretching said rod at a temperature above its $T_g$ to a final length which is at least twice that of its initial length;
   (c) allowing said stretched rod to cool to a temperature below its $T_g$ and re-solidify in its stretched form;
   (d) cutting said stretched rod to an appropriate length so that at least two plugs can be fashioned from the same rod;
   (e) sharpening one end of said stretched rod so that it is tapered.

42. The process of claim 41 wherein said polymeric material is selected from the group consisting of polymers, homopolymers, cross-linked polymers and copolymers of silicones, acrylic esters, polyurethanes, hydrocarbon polymers and combinations thereof.

43. The process of claim 42 wherein said polymeric material is an acrylic ester.

44. The process of claim 41 wherein said polymeric material has a $T_g$ of less than about 37° C.

45. The process of claim 44 wherein said polymeric material is a copolymer of polymethylmethacrylate and polylaurylmethacrylate.

* * * * *